United States Patent [19]

Neustadt et al.

[11] 4,379,166

[45] Apr. 5, 1983

[54] ARYLMETHOXY-, ARYLMETHYLTHIO-, HETEROARYLMETHOXY-, AND HETEROARYLMETHYLTHIO-ALKYLAMINOALCOHOLS

[75] Inventors: Bernard R. Neustadt; Elijah H. Gold, both of West Orange, N.J.

[73] Assignee: Schering Corporation, Kenilworth, N.J.

[21] Appl. No.: 289,339

[22] Filed: Aug. 3, 1981

[51] Int. Cl.[3] .............. A61K 31/165; A61K 31/135; C07D 253/08; C07D 217/18

[52] U.S. Cl. .................................. 424/324; 424/330; 564/162; 564/164; 564/165; 564/340; 564/363; 544/183; 544/237; 544/238; 544/283; 544/335; 544/336; 544/353; 546/149; 546/176; 546/309; 546/312; 548/260; 548/261; 548/342; 548/378; 548/561

[58] Field of Search ............ 564/363, 340, 162, 164, 564/165; 424/324, 330; 544/237, 335, 238, 336, 353, 183, 283; 548/260, 261, 378, 342; 260/326.41, 326.47, 326.5 S, 326.5 SF; 546/309, 312, 176, 149

[56] References Cited

U.S. PATENT DOCUMENTS

| | | | |
|---|---|---|---|
| 4,000,192 | 12/1976 | Lunts et al. | 564/165 |
| 4,000,193 | 12/1976 | Lunts et al. | 564/165 |
| 4,012,444 | 3/1977 | Lunts et al. | 564/165 |

FOREIGN PATENT DOCUMENTS 1200886  8/1970  United Kingdom ............... 564/165

*Primary Examiner*—Delbert R. Phillips
*Assistant Examiner*—Frederick W. Pepper
*Attorney, Agent, or Firm*—Anita W. Magatti; Bruce M. Eisen

[57] ABSTRACT

This invention relates to 5-(2-alkylamino-1-hydroxyethyl)salicylamides and 4-(2-alkylamino-1-hydroxyethyl)-2-(methylsulfinyl)phenols wherein the alkyl group is substituted by arylmethoxy, arylmethylthio, heteroarylmethoxy, or heteroarylmethylthio, pharmaceutical compositions thereof, and their use as cardiovascular agents.

14 Claims, No Drawings

ARYLMETHOXY-, ARYLMETHYLTHIO-, HETEROARYLMETHOXY-, AND HETEROARYLMETHYLTHIO-ALKYLAMINOALCOHOLS

The present invention relates to novel compositions-of-matter, to pharmaceutical compositions thereof, and to methods for their use.

More particularly, this invention relates to 5-(2-alkylamino-1-hydroxyethyl)salicylamides and 4-(2-alkylamino-1-hydroxyethyl)-2-(methylsulfinyl)phenols, wherein the alkyl group is substituted by arylmethoxy, arylmethylthio, heteroarylmethoxy, or heteroarylmethylthio. Also included are pharmaceutical compositions thereof, and methods for their use as cardiovascular agents.

Specifically, this invention relates to compounds of the formula

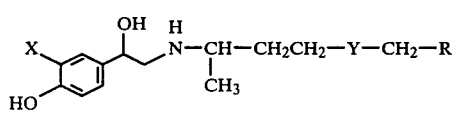

wherein

X is carbamoyl, mono- and dialkyl carbamoyl, alkylthio, alkylsulfinyl, or alkylsulfonyl;

Y is O, S, SO, or $SO_2$;

R is phenyl; phenyl substituted by alkyl, hydroxy, alkoxy, halo, carboxy, alkoxycarbonyl or nitro groups; heteroaryl groups having 5 to 10 ring members having one or two rings comprising aromatic carbon atoms and from 1 to 3 nitrogen atoms, and substituted derivatives thereof wherein said heteroaryl group is substituted by alkyl, hydroxy, alkoxy, halo, phenyl or alkoxycarbonyl;

and the pharmaceutically acceptable salts thereof.

The alkyl groups referred to above preferably contain 1 to 6 carbon atoms and include methyl, ethyl, propyl, butyl, pentyl, hexyl and the corresponding branched chain isomers thereof. The alkoxy groups likewise preferably contain 1 to 6, and most preferably 1 to 3, carbon atoms and are illustrated by methoxy, ethoxy, propoxy, isopropoxy and the like.

Alkoxycarbonyl groups contain alkoxy groups as defined above attached to a carbonyl group: examples are methoxycarbonyl, ethoxycarbonyl and propoxycarbonyl.

The halogen atoms may be fluorine, chlorine, bromine or iodine.

The heteroaryl group as defined above may contain one or two rings of 5 to 10 ring members comprising aromatic carbon atoms and from 1 to 3 nitrogen atoms, examples being imidazolyl, triazolyl, pyridyl, pyridazyl, pyrimidyl, pyrazyl, triazyl, quinolyl, isoquinolyl, quinazoyl, quinoxalyl, pyrrolyl, pyrazolyl, phthalazyl, 1,2,4-benzotriazyl, and benzotriazolyl. The substituents on the heteroaryl groups may be 1 to 3 of the groups indicated above. Where positional isomers occur, all are contemplated, i.e., 2-pyridyl, 3-pyridyl, and 4pyridyl.

The pharmaceutically acceptable salts may be derived from a variety of organic and inorganic acids such as sulfuric, phosphoric, hydrochloric, hydrobromic, hydroiodic, sulfamic, citric, lactic, maleic, succinic, tartaric, cinnamic, acetic, benzoic, gluconic, ascorbic and related acids.

Preferred compounds of formula I are those wherein X is carbamoyl or methylsulfinyl. Especially preferred are those wherein Y is oxygen or sulfur, and particularly preferred are compounds of formula I wherein Y is oxygen.

The compounds of formula I are conveniently prepared by reaction of a compound of the formula II

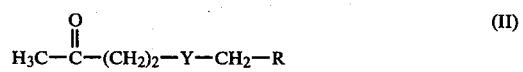

wherein Y and R are as hereinbefore defined, with the appropriate compound of the formula III

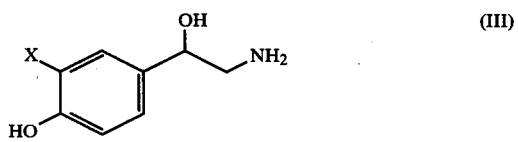

wherein X is as hereinbefore defined, in the presence of a reducing agent. The reaction is typically conducted in an organic solvent, with lower alkanols such as methanol, ethanol and 2-propanol being preferred. Sodium cyanoborohydride is a highly preferred reducing agent, but others, such as sodium borohydride, may also be utilized.

A further method for the preparation of the compounds of formula I involves the reaction of an amine of the formula IV

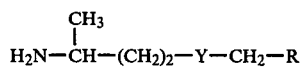

wherein Y and R are as hereinbefore defined, with a haloketone of the formula V

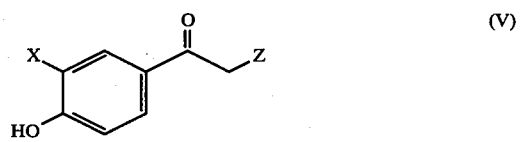

wherein Z is chloro or bromo, and X is as hereinbefore defined, in a suitable solvent in the presence of an acid acceptor to give the intermediate of the formula VI

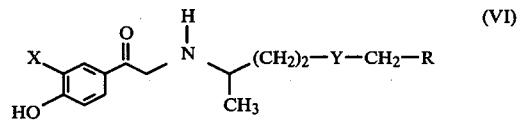

wherein X, Y, and R are as hereinbefore defined. The acid acceptor may be an organic base such as pyridine or triethylamine, or an inorganic base such as sodium or potassium carbonate.

The resultant compound of formula VI is then reduced to afford the compounds of formula I. A particularly suitable reducing agent for this process is sodium borohydride, but other common ketone reducing agents, such as lithium borohydride and potassium borohydride, may also be utilized.

The compounds of formula I wherein X is methylsulfinyl or methylsulfonyl or those where Y is sulfinyl or sulfonyl are preparable by oxidation of the corresponding compound of formula I wherein X is methyl thio or Y is thio with a suitable oxidizing agent much as peracetic acid. The sulfinyl compounds are obtained by employing only a slight stoichiometric excess of the peracid, while use of more than two equivalents of the oxidizing agent results in the sulfonyl compounds. Alternatively, this oxidation may be performed at any stage of the synthetic sequence to ultimately afford the desired compounds.

The compounds of this invention are produced by the foregoing methods as stereoisomeric mixtures, i.e., they possess one or more asymmetric carbon and sulfur atoms and therefore exist as chiral mixtures. The compounds may be used as stereoisomeric mixtures or separated into their enantiomeric and diastereomeric pairs or their pure chiral forms using conventional methods for the separation of such mixtures, such as fractional crystallization and chromatography. In addition, a desired enantiomer may be obtained utilizing pure chiral starting materials. In general, preferred compounds possess the R configuration at both chiral carbon atoms.

The following compounds may be prepared by the above processes and are representative of the invention:
2-(4-benzyloxy-2-butylamino)-1-(4-hydroxy-3-methylsulfinylphenyl)ethanol,
2-(4-(4-bromobenzyloxy)-2-butylamino)-1-(4-hydroxy-3-methylsulfinylphenyl)ethanol,
2-(4-(4-methoxybenzyloxy)-2-butylamino)-1-(4-hydroxy-3-methylsulfinylphenyl)ethanol,
2-(4-(4-nitrobenzyloxy)-2-butylamino)-1-(4-hydroxy-3-methylsulfinylphenyl)ethanol,
2-(4-(4-methylbenzyloxy)-2-butylamino)-1-(4-hydroxy-3-methylsulfinylphenyl)ethanol,
2-(4-(4-hydroxybenzyloxy)-2-butylamino)-1-(4-hydroxy-3-methylsulfinylphenyl)ethanol,
2-(4-(4-carboxybenzyloxy)-2-butylamino)-1-(4-hydroxy-3-methylsulfinylphenyl)ethanol,
2-(4-(4-ethoxycarbonylbenzyloxy)-2-butylamino)-1-(4-hydroxy-3-methylsulfinylphenyl)ethanol,
the 4-benzylthio analogs thereof, and the analogs wherein methylsulfinyl is replaced by carbamoyl for both the oxo and thio compounds;
2-(4-(3-p yridylmethoxy)-2-butylamino)-1-(4-hydroxy-3-methylsulfinylphenyl)ethanol,
2-(4-(5-pyrimidylmethoxy)-2-butylamino)-1-(4-hydroxy-3-methylsulfinylphenyl)ethanol,
2-(4-imidazolylmethoxy)-2-butylamino)-1-(4-hydroxy-3-methylsulfinylphenyl)ethanol,
2-(4-(3-quinolylmethoxy)-2-butylamino)-1-(4-hydroxy-3-methylsulfinlyphenyl)ethanol,
the heteroarylmethylthio analogs thereof (i.e. compounds of formula I wherein Y is S and R is heteroaryl), and the analogs wherein methylsulfinyl is replaced by carbamoyl for both the oxo and thio compounds;
2-(4-(6-methyl-3-pyridylmethoxy)-2-butylamino)-1-(4-hydroxy-3-methylsulfinylphenyl)ethanol,
2-(4-(5-hydroxy-3-pyridylmethoxy)-2-butylamino)-1-(4-hydroxy-3-methylsulfinylphenyl)ethanol,
2-(4-(6-methoxy-3-pyridylmethoxy)-2-butylamino)-1-(4-hydroxy-3-methylsulfinylphenyl)ethanol,
2-(4-(4-chloro-3-pyridylmethoxy)-2-butylamino)-1-(4-hydroxy-3-methylsulfinylphenyl)ethanol,
2-(4-(5-phenyl-3-pyridylmethoxy)-2-butylamino)-1-(4-hydroxy-3-methylsulfinylphenyl)ethanol,
2-(4-(4-ethoxycarbonyl-3-pyridylmethoxy)-2-butylamino)-1-(4-hydroxy-3-methylsulfinylphenyl)ethanol,
the heteroarylmethylthio analogs thereof (i.e. compounds of formula I wherein Y is S and R is heteroaryl),
the analogs wherein methylsulfinyl is replaced by carbamoyl for both the oxo and thio compounds, and other heteroaryl compounds of formula I, e.g. wherein R is 2-methoxy-5-pyrimidyl, 2-methyl-4-imidazolyl or 2-methyl-3-quinolyl, and Y is O or S.

The starting materials of formula II are prepared by reaction of a compound of formula VII

HY—CH₂—R  (VII)

wherein Y and R are as hereinbefore defined, with methyl vinyl ketone in the presence of an acid, preferably sulfuric acid. The reaction is preferably carried out at room temperature, with reaction times varying from 1 hour to 7 days.

Alternatively, the compound of formula VII can be reacted in the presence of base with a compound of formula VIII.

(VIII)

wherein W is chloro, bromo, alkanesulfonyloxy, or arenesulfonyloxy, to produce a compound of formula IX

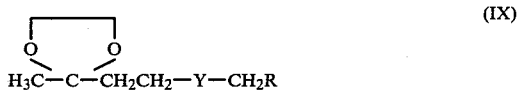

(IX)

wherein Y and R are as hereinbefore defined. The intermediate IX is treated with hydrochloric acid, with or without an organic co-solvent, to produce a compound of formula II. Typical reaction times are 1–20 hours at room temperature.

For compounds of formula I wherein X is methylsulfinyl, a novel preferred method of preparing the intermediates of formula III wherein X is methylsulfinyl comprises:

(a) bromination of 4-hydroxy-3-methylthio acetophenone in an organic solvent such as chloroform, followed by;

(b) treatment with sodium azide in an organic solvent such as tetrahydrofuran to produce 2-azido-4'-hydroxy-3'-methylthioacetophene;

(c) reduction of the keto group in the azido product of step (b) in a non-reactive organic solvent such as chloroform: ethanol with a reducing agent, typically sodium borohydride, to obtain 2-azido-1-(4-hydroxy-3-methylthiophenyl)ethanol;

(d) treatment of the product of step (c) with 1,3-propane dithiol and triethylamine in an organic solvent, e.g., a lower alkanol such as methanol or ethanol, to give 2-amino-1-(4-hydroxy-3-methylthiophenyl)ethanol;

(e) oxidation of methylthiophenyl compound with peracetic acid in a lower alkanol to produce 2-amino-1-(4-hydroxy-3-methylthiophenyl)ethanol.

The resultant compound of formula III may be reacted with a compound of formula II to produce a compound of formula I wherein X is methylsulfinyl.

The starting materials of formula III are also produced by hydrogenation of the corresponding compound of formula XI

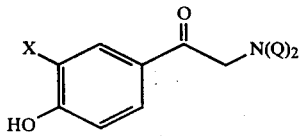

(XI)

wherein X is as hereinbefore defined and Q is an amino blocking group removable by hydrogenation. Typical blocking groups are those such as benzyl and benzhydryl. The hydrogenation is usually and preferably conducted in a lower alkanol solvent, such as methanol, in the presence of a catalyst. Suitable catalysts are those such as palladium and palladium-on-carbon. Typical reaction times vary from 8–24 hours.

The starting materials of formulae IV, V, VII, VIII, and XI are either known in the art or preparable by processes analogous to those known in the art.

The compounds of this invention are useful in view of their pharmacological properties. In particular, they possess activity as antihypertensive agents as evidenced by their ability to reduce blood pressure in animals in which the blood pressure has become abnormally elevated.

The antihypertensive activity of the instant compounds is demonstrated by the results of a standardized test for such activity using male, spontaneously hypertensive rats in which systolic blood pressures and heart rates are recorded by the semi-automated indirect procedure of Vaynofski. Among the compounds of this invention which have been found particularly active in this test are the representative compounds, 2-(4-(4-methoxybenzyloxy)-2-butylamino)-1-(4-hydroxy-3-methylsulfinylphenyl)ethanol, 2-(4-benzyloxy-2-butylamino)-1-(4-hydroxy-3-methylsulfinylphenyl)ethanol, 5-(2-(4-benzyloxy-2-butylamino)-1-hydroxyethyl)-salicylamide and 5-(2-(4-(4-methoxybenzyloxy)-2-butylamino)-1-hydroxyethyl)salicylamide.

In view of their potent pharmacological properties, the compounds of this invention can be combined with pharmaceutical carriers and administered in a variety of well known pharmaceutical forms suitable for oral or parenteral administration to provide compositions useful in the treatment of cardiovascular disorders and particularly mammalian hypertension.

Based upon laboratory tests, the effective dose ($ED_{50}$) of the compounds of this invention will typically be in the range of about 0.5 to about 100 mg/kg, preferably 1–10 mg/kg, of mammalian weight, administered in single or divided doses. The exact dose to be administered is dependent upon where the particular compound lies within the above quoted range, as well as upon the age, weight and condition of the individual.

The composition containing the compounds of this invention will preferably contain from about 5 to about 250 mg. of the active compound per dosage unit. These compositions are most preferably administered orally. Typical formulations for oral administration are those such as tablets, capsules, syrups, elixirs or suspensions. Typical injectable formulations include solutions and suspension.

Typical acceptable pharmaceutical carriers for use in the formulations described above are exemplified by: sugars such as lactose, sucrose, mannitol and sorbitol; starches such as corn starch, tapioca starch and potato starch; cellulose and derivatives such as sodium carboxymethyl cellulose, ethyl cellulose and methyl cellulose; calcium phosphates such as dicalcium phosphate and tricalcium phosphate; sodium sulfate; calcium sulfate, polyvinylpyrrolidone, polyvinyl alcohol; stearic acid; alkaline earth metal stearates such as magnesium stearate and calcium stearate; stearic acid vegetable oils such as peanut oil, cottonseed oil, sesame oil, olive oil and corn oil; non-ionic, cationic and anionic surfactants; ethylene glycol polymers; beta-cyclodextrin; fatty alcohols and hydrolyzed cereal solids; as well as other non-toxic compatible fillers, binders, disintegrants and lubricants commonly used in pharmaceutical formulations.

In treating certain patients with the compounds of this invention, it may be desirable to include other pharmaceutically active ingredients in the same dosage unit. For example, in treating patients in whom salt and water retention is a problem, effective amounts of conventional diuretics, e.g., hydrochlorothiazide or trichloromethiazide, may be added.

The following examples describe in detail compounds and compositions illustrative of the present invention and methods which have been devised for their preparation. It will be apparent to those skilled in the art that many modifications, both of materials and methods, may be practiced without departing from the purpose and intent of this disclosure.

PREPARATION 1

5-(2-AMINO-1-HYDROXYETHYL)SALICYLAMIDE

To 5-[2-(dibenzylamino)acetyl]salicylamide (75.0 g, 0.200 mmol) and acetic acid (24.0 g, 0.40 mmol) in 1.0 liter methanol, add 5% palladium/carbon (40.0 g). Hydrogenate at 3 atmospheres for 16 hours. Filter the catalyst, concentrate slightly and adjust the volume to give a solution of the title compound of the desired molarity.

PREPARATION 2

4-(4-METHOXYBENZYLOXY)-2-BUTANONE

Combine 4-methoxybenzyl alcohol (13.8 g, 0.10 mole) with methyl vinyl ketone (8.4 g, 0.12 mole), treat with 5 drops of concentrated sulfuric acid, and stir 1 hour. Dilute with ethyl ether, wash with 1.0 N sodium bicarbonate solution, dry the organic phase over anhydrous sodium sulfate and evaporate in vacuo to obtain the title compound, m.p. 48–9° C.

PREPARATION 3

4-(4-NITROBENZYLOXY)-2-BUTANONE

Treat 4-nitrobenzyl alcohol with methyl vinyl ketone in a manner similar to Preparation 2 to obtain the title compound.

PREPARATION 4

2-AMINO-1-(4-HYDROXY-3-METHYLSULFINYLPHENYL)ETHANOL

A. Add bromine (96.0 g, 0.6 mole) in chloroform (350 ml) dropwise to 4-hydroxy-3-methylthioacetophenone (109.2 g, 0.6 mole) in chloroform (1600 ml). Wash with 1.0 N sodium bicarbonate solution, dry the organic layer over sodium sulfate and evaporate in vacuo to obtain 2-bromo-4'-hydroxy-3'-methylthioacetophenone, mp. 118°–120° C.

B. To a solution of the product of Step A (150.5 g, 0.576 mole) in tetrahydrofuran (1 liter) cooled to 20° C., add dropwise sodium azide (37.4 g, 0.576 mole) in water (450 ml) and stir for five hours. Partially evaporate the solvent and extract the concentrated reaction mixture with chloroform. Dry the organic phase and evaporate in vacuo to obtain 2-azido-4′-hydroxy-3′-methylthioacetophenone, mp. 124°–129° C.

C. Dissolve the product of Step B (58.8 g, 0.263 mole) in chlorform (1 liter) and ethanol (1 liter), add sodium borohydride (9.99 g, 0.263 mole) and allow to stand 16 hours. Concentrate the resultant mixture and extract with ethyl acetate/1.0 N sodium bicarbonate solution. Dry the organic layer over sodium sulfate and evaporate in vacuo to obtain 2-azido-1-(4-hydroxy-3-methylthiophenyl)ethanol.

D. Stir the product of Step C (49.5 g, 0.22 mole), 1,3-propane dithiol (103.6 g, 0.96 mole) and triethylamine (101.0 g, 1.0 mole) in methanol (1500 ml) for 72 hours. Cool to 0° C., filter and evaporate in vacuo to obtain 2-amino-1-(4-hydroxy-3-methylthiophenyl)ethanol.

E. To the product of Step D (0.22 mol) in methanol (800 ml) at 0° C., add dropwise a solution of peracetic acid (42 ml of a 40% solution, 0.22 mole) in methanol (70 ml). Evaporate to obtain 2-amino-1-(4-hydroxy-3-methylsulfinylphenyl)ethanol acetate salt.

PREPARATION 5

4-(HETEROARYLMETHOXY)-2-BUTANONES

In a manner similar to that described in Preparation 2, treat each of 4-imidazolemethanol, 3-pyridinemethanol, 5-pyrimidine methanol, 3-quinolinemethanol, 6-methoxy-3-pyridinemethanol, and 2-methoxy-5-pyrimidine methanol with methyl vinyl ketone to obtain the following:
A. 4-(4-imidazolylmethoxy)-2-butanone,
B. 4-(3-pyridylmethoxy)-2-butanone,
C. 4-(5-pyrimidylmethoxy)-2-butanone,
D. 4-(3-quinolylmethoxy)-2-butanone,
E. 4-(6-methoxy-3-pyridylmethoxy)-2-butanone, and
F. 4-(2-methoxy-5-pyrimidylmethoxy)-2-butanone.

EXAMPLE I

5-(2-(4-(ARYLMETHOXY OR ARYLMETHYLTHIO)-2-BUTYLAMINO)-1-HYDROXYETHYL)SALICYAMIDES

A.
5-(2-(4-Benzyloxy-2-Butylamino)-1-Hydroxyethyl)-Salicylamide

Combine 4-benzyloxy-2-butanone (2.6 g, 15 mmol) with 5-(2-amino-1-hydroxyethyl)salicylamide (15 mmol in methanol, 50 ml) and treat with sodium cyanoborohydride (0.9 g, 15 mmol). Let stand 16 hours, evaporate the solvent and extract the residue in ethyl acetate/ 1N sodium bicarbonate solution. Separate the organic phase, dry over sodium sulfate and evaporate in vacuo. Crystallize the resultant residue from acetonitrile to obtain the title compound, m.p. 123°–4° C.

B. In a similar manner, treat each of 4-benzylthio-2-butanone, 4-(4-methoxybenzyloxy)-2-butanone, and 4-(4-nitrobenzyloxy)-2-butanone with 5-(2-amino-1-hydroxyethyl)salicylamide to obtain the following:
1. 5-(2-(4-(4-benzylthio-2-butylamino)-1-hydroxyethyl)-salcylamide, m.p. 116°–120° C.;
2. 5-(2-(4-methoxybenzyloxy)-2-butylamino)-1-hydroxyethyl)salicylamide, m.p. 110°–114° C.; and
3. 5-(2-(4-(4-nitrobenzyloxy)-2-butylamino)-1-hydroxyethyl)salicylamide.

EXAMPLE II

2-[4-(ARYLMETHOXY OR ARYLMETHYLTHIO)-2-BUTYLAMINO]-1-(4-HYDROXY-3-METHYLSULFINYLPHENYL)ETHANOL

A.
2-(4-Benzyloxy-2-Butylamino)-1-(4-Hydroxy-3-Methylsulfinylphenyl)Ethanol

Combine 4-benzyloxy-2-butanone (1.78 g, 10 mmol) with 2-amino-1-(4-hydroxy-3-methylsulfinylphenyl)ethanol (10 mmol) in methanol (50 ml) and add sodium cyanoborohydride (0.63 g, 10 mmol). Let stand 16 hours, concentrate the solution and purify the crude product by chromatography on silica gel using chloroform: methanol: ammonium hydroxide (70:27:3) as eluent to obtain the title compound.

B. In a similar manner, treat each of 4-(4-methoxybenzyloxy)-2-butanone, 4-benzylthio-2-butanone and 4-nitro benzyloxy-2-butanone to obtain the following:
1. 2-(4-(4-methoxybenzyloxy)-2-butylamino)-1-(4-hydroxy-3-methylsulfinylphenyl)ethanol,
2. 2-(4-benzylthio-2-butylamino)-1-(4-hydroxy-3-methylsulfinylphenyl)ethanol, and
3. 2-(4-(4-nitrobenzyloxy)-2-butylamino)-1-(4-hydroxy-3-methylsulfinylphenyl)ethanol.

EXAMPLE III

5-(2-(4-(HETEROARYLMETHOXY OR HETEROARYLMETHYLTHIO)-2-BUTYLAMINO)-1-HYDROXYETHYL)-SALICYLAMIDES

A.
5-(2-(4-Heteroarylmethoxy-2-Butylamino)-1-Hydroxyethyl)Salicylamides

In a manner similar to that described in Example IA, treat the heteroarylmethoxy-2-butanones prepared in Preparation 5 with 5-(2-amino-1-hydroxyethyl)salicylamide to obtain the following compounds:
1. 5-(2-(4-imidazolylmethoxy)-2-butylamino)-1-hydroxyethyl)salicylamide,
2. 5-(2-(4-(3-pyridylmethoxy)-2-butylamino)-1-hydroxyethyl)salicylamide,
3. 5-(2-(4-(5-pyrimidylmethoxy)-2-butylamino)-1-hydroxyethyl)salicylamide,
4. 5-(2-(4-(3-quinolylmethoxy)-2-butylamino)-1-hydroxyethyl)salicylamide,
5. 5-(2-(4-(6-methoxy-3-pyridylmethoxy)-2-butylamino)-1-hydroxyethyl)salicylamide, and
6. 5-(2-(4-(2-methoxy-5-pyrimidylmethoxy)-2-butylamino)-1-hydroxyethyl)salicylamide.

B.
5-(2-(4-Heteroarylmethylthio-2-Butylamino)-1-Hydroxyethyl)Salicylamides

In a manner similar to that described in Example IA, treat each of 4-(3-pyridylmethylthio)-2-butanone and 4-(β-quinolylmethylthio)-2-butanone with 5-(2-amino-1-hydroxyethyl)salicylamide to obtain the following compounds:
1. 5-(2-(3-pyridylmethylthio)-2-butylamino)-1-hydroxyethyl)salicylamide, and 2. 5-(2-(4-(3-quinolylmethylthio)-2-butylamino)-1-hydroxyethyl)salicylamide.

EXAMPLE IV

2-(4-(HETEROARYLMETHOXY OR HETEROARYLMETHYLTHIO)-2-BUTYLAMINO)-1-(4-HYDROXY-3-METHYLSULFINYLPHENYL)ETHANOLS

A.
2-(4-Heteroarylmethoxy-2-Butylamine)-1-(4-Hydroxy-3-Methylsulfinylphenyl)Ethanols In a manner similar to that described in Example II-A, treat the heteroarylmethoxy-2-butanones prepared in Preparation 5 with 2-amino-1-(4-hydroxy-3-methylsulfinylphenyl)ethanol to obtain the following compounds:
1. 2-(4-imidazolylmethoxy-2-butylamino)-1-(4-hydroxy-3-methylsulfinylphenyl)ethanol,
2. 2-(3-(3-pyridylmethoxy)-2-butylamino)-1-(4-hydroxy-3-methylsulfinylphenyl)ethanol,
3. 2-(4-(5-pyrimidylmethoxy)-2-butylamino)-1-(4-hydroxy-3-methylsulfinylphenyl)ethanol,
4. 2-(4-(3-quinolylmethoxy)-2-butylamino)-1-(4-hydroxy-3-methylsulfinylphenyl)ethanol,
5. 2-(4-(6-methoxy-3-pyridylmethoxy)-2-butylamino)-1-(4-hydroxy-3-methylsulfinyl phenyl)ethanol, and
6. 2-(4-(2-methoxy-5-pyrimidylmethoxy)-2-butylamino)-1-(4-hydroxy-3-methylsulfinylphenyl)ethanol.

B.
2-(4-Heteroarylmethylthio-2-Butylamino)-1-(4-Hydroxy-3-Methylsulfinylphenyl)Ethanols In a manner similar to that described in Example II-A, treat each of 4-(3-pyridylmethylthio)-2-butanone and 4-(3-quinolylmethylthio)-2-butanone with 2-amino-1-(4-hydroxy-3-methylsulfinylphenyl)ethanol to obtain the following compounds:
1. 2-(4-(3-pyridylmethylthio)-2-butylamino)-1-(4-hydroxy-3-methylsulfinylphenyl)ethanol, and
2. 2-(4-(3-quinolylmethylthio)-2-butylamino)-1-(4-hydroxy-3-methylsulfinylphenyl)ethanol.

In the following examples, the active ingredient is preferably 2-(4-(4-methoxybenzyloxy)-2-butylamino)-1-(4-hydroxy-3-methylsulfinylphenyl)ethanol, 2-(4-benzyloxy-2-butylamino)-1-(4-hydroxy-3-methylsulfinylphenyl)-ethanol, 5-(2-(4-benzyloxy-2-butylamino)-1-hydroxyethyl)salicylamide, or 5-(2-(4-(4-methoxybenzyloxy)-2-butylamino)-1-hydroxyethyl)salicylamide, but an equivalent quantity of another compound (or more than one compound) of formula I, especially a compound named herein, may be substituted:

EXAMPLE V

| Capsule | Amount (mg) | |
|---|---|---|
| Active ingredient | 250.0 | 125.0 |
| Lactose | 173.0 | 86.5 |
| Corn Starch | 75.0 | 37.5 |
| Magnesium Sterate | 2.0 | 1.0 |
| | 500.0 | 250.0 |

Blend the active ingredient, lactose and corn starch until uniform; then blend the magnesium sterate into the resulting powder. Encapsulate the mixture into suitable sized two-piece hard gelatine capsules.

EXAMPLE VI

| Tablet | Amount (mg) | |
|---|---|---|
| Active ingredient | 250.0 | 125.0 |
| Lactose | 161.0 | 80.5 |
| Corn Starch | 12.0 | 6.0 |
| Water (per thousand tablets) | 120 ml (evaporates) | 60 ml (evaporates) |
| Corn Starch | 75.0 | 37.5 |
| Magnesium Sterate | 2.0 | 1.0 |
| | 500.0 | 250.0 |

Blend the active ingredient with the lactose until uniform. Blend the smaller quantity of corn starch with the water and add the resulting corn starch paste, then mix until a uniform wet mass is formed. Add the remaining corn starch to the wet mass and mix until uniform granules are obtained. Screen the granules through a suitable milling machine, using a ¾" stainless steel screen. Dry the milled granules in a suitable drying oven until the desired moisture content is obtained. Mill the dried granules through a suitable milling machine using 16 mesh stainless steel screen. Blend the magnesium sterate and compress the resulting mixture into tablets of desired shape, thickness, hardness and disintergration.

EXAMPLE VII

| Injectable Solution | mg/ml |
|---|---|
| Active ingredient | 5.00 |
| Methyl p-hydroxybenzoate | 0.80 |
| Propyl p-hydroxybenzoate | 0.10 |
| Disodium Edetate | 0.10 |
| Citric Acid Monohydrate | 0.08 |
| Dextrose | 40.00 |
| Water for injection qs ad | 1.0 ml |

Dissolve the p-hydroxybenzoates in a portion of water for injection at 60°–70° C., and cool the solution to 25°–35° C. Charge and dissolve all other excipients and the active ingredient. Bring the solution to final volume, filter it through a sterilizing membrane and fill into sterile containers.

We claim:
1. A compound of the formula

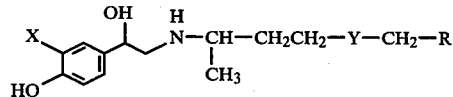

wherein
X is carbamoyl, mono- or di- $C_1$ to $C_6$ alkyl carbamoyl, $C_1$ to $C_6$ alkylthio, $C_1$ to $C_6$ alkylsulfinyl, or $C_1$ to $C_6$ alkylsulfonyl;
Y is O, S, SO, or $SO_2$; and
R is phenyl; phenyl substituted by $C_1$ to $C_6$ alkyl, hydroxy, $C_1$ to $C_6$ alkoxy, halo, carboxy, $C_1$ to $C_6$ alkoxycarbonyl, or nitro groups; heteroaryl groups having 5 to 10 ring members having one or two rings comprising aromatic carbon atoms and from 1 to 3 nitrogen atoms, and substituted derivatives thereof wherein said heteroaryl group is substituted by $C_1$ to $C_6$ alkyl, hydroxy, $C_1$ to $C_6$ alkoxy, halo, phenyl, or $C_1$ to $C_6$ alkoxycarbonyl, and wherein said heteroaryl group is joined to the side chain at one of said ring aromatic carbon atoms; and the pharmaceutically acceptable salts thereof.

2. A compound according to claim 1 wherein X is carbamoyl.

3. A compound according to claim 1 wherein X is methylsulfinyl.

4. A compound according to claim 2 or 3 wherein Y is O.

5. A compound according to claim 2 or 3 wherein Y is S.

6. A compound according to claim 4 wherein R is 4-methoxyphenyl.

7. A compound according to claim 4 wherein R is phenyl.

8. A compound according to claim 6 wherein X is methylsulfinyl, said compound being 2-(4-(4-methoxybenzyloxy)-2-butylamino)-1-(4-hydroxy-3-methylsulfinylphenyl)ethanol.

9. A compound according to claim 6 wherein X is carbamoyl, said compound being 5-(2-(4-(4-methoxybenzyloxy)-2-butylamino)-1-hydroxyethyl)salicylamide.

10. A compound according to claim 7 wherein X is methylsulfinyl, said compound being 2-(4-benzyloxy-2-butylamino)-1-(4-hydroxy-3-methylsulfinylphenyl)ethanol.

11. A compound according to claim 7 wherein X is carbamoyl, said compound being 5-(2-(4-benzyloxy-2-butylamino)-1-hydroxyethyl) salicylamide.

12. A pharmaceutical composition comprising an effective antihypertensive amount of a compound of claim 1 together with a non-toxic pharmaceutically acceptable carrier.

13. A method of eliciting an antihypertensive response comprising administering to a hypertensive mammal a composition of claim 12.

14. A compound of claim 1 wherein both chiral carbon atoms are of the R configuration.

* * * * *